United States Patent
Wegener et al.

(10) Patent No.: US 7,916,830 B2
(45) Date of Patent: Mar. 29, 2011

(54) EDGE DETECTION FOR COMPUTED TOMOGRAPHY PROJECTION DATA COMPRESSION

(75) Inventors: Albert W. Wegener, Portola Valley, CA (US); Yi Ling, Redwood City, CA (US)

(73) Assignee: Samplify Systems, Inc., Santa Clara, CA (US)

( * ) Notice: Subject to any disclaimer, the term of this patent is extended or adjusted under 35 U.S.C. 154(b) by 130 days.

(21) Appl. No.: 12/208,835

(22) Filed: Sep. 11, 2008

(65) Prior Publication Data

US 2010/0061505 A1    Mar. 11, 2010

(51) Int. Cl.
    *A61B 6/00* (2006.01)
(52) U.S. Cl. .......................... 378/19; 382/232
(58) Field of Classification Search ............... 378/19; 382/232
    See application file for complete search history.

(56) References Cited

U.S. PATENT DOCUMENTS

| | | | |
|---|---|---|---|
| 4,982,415 A | 1/1991 | Shibata et al. | |
| 5,055,821 A | 10/1991 | Keller et al. | |
| 5,204,943 A | 4/1993 | Watanabe et al. | |
| 5,357,549 A * | 10/1994 | Maack et al. | 378/62 |
| 5,615,287 A * | 3/1997 | Fu et al. | 382/232 |
| 5,703,965 A | 12/1997 | Fu et al. | |
| 6,144,772 A | 11/2000 | Garland et al. | |
| 6,195,462 B1 * | 2/2001 | Bryniarski et al. | 382/239 |
| 6,259,761 B1 | 7/2001 | Lai | |
| 6,292,919 B1 | 9/2001 | Fries et al. | |
| 6,327,327 B1 | 12/2001 | Herold et al. | |
| 6,343,109 B2 | 1/2002 | Doubrava et al. | |
| 6,433,631 B2 | 8/2002 | Pearson, Jr. et al. | |
| 6,470,065 B1 | 10/2002 | Lauther | |
| 6,560,307 B2 | 5/2003 | Marume | |
| 6,608,915 B2 * | 8/2003 | Tsujii | 382/132 |
| 6,671,755 B1 | 12/2003 | Leahy et al. | |
| 6,914,957 B2 | 7/2005 | Dafni et al. | |
| 7,240,251 B2 | 7/2007 | Popescu | |
| 7,248,641 B2 | 7/2007 | Schilling et al. | |
| 7,254,210 B2 | 8/2007 | Popescu | |
| 7,274,765 B2 | 9/2007 | Krumme et al. | |

(Continued)

FOREIGN PATENT DOCUMENTS

JP    58019238    2/1983

(Continued)

OTHER PUBLICATIONS

Hashimoti, Masayuki, et al., "CT Image Compression with Level of Interest," 2004 IEEE Int'l Conf. on Image Processing (ICIP), 4 pages.

(Continued)

*Primary Examiner* — Edward J Glick
*Assistant Examiner* — Alexander H Taningco
(74) *Attorney, Agent, or Firm* — Carolyn Koenig; Haynes Beffel & Wolfeld LLP

(57) ABSTRACT

A compression subsystem for a computed tomography system compresses projection data to for efficient data transfer and storage. The compression includes detecting edges in the projection data corresponding to the object being imaged to set boundaries for compression operations. The edge detection compares difference samples to positive and negative thresholds to determine the boundaries. The projection samples or the difference samples are compressed between the boundaries. The boundaries are encoded and included in the compressed data. The compressed samples are decompressed prior to image reconstruction processing. Decompression includes decoding the compressed samples and the boundary values. This abstract does not limit the scope of the invention as described in the claims.

26 Claims, 8 Drawing Sheets

U.S. PATENT DOCUMENTS

| | | |
|---|---|---|
| 7,327,866 B2 | 2/2008 | Bae et al. |
| 7,502,438 B2 | 3/2009 | Nakagawa et al. |
| 7,653,252 B2 * | 1/2010 | Hernandez et al. ............ 382/232 |
| 2002/0031277 A1 * | 3/2002 | Lubin et al. .................... 382/254 |
| 2002/0057827 A1 * | 5/2002 | Nagata et al. .................. 382/131 |
| 2002/0057844 A1 * | 5/2002 | Sirohey et al. ................ 382/240 |
| 2003/0199757 A1 | 10/2003 | Toth et al. |
| 2003/0228041 A1 | 12/2003 | Bae et al. |
| 2004/0022447 A1 * | 2/2004 | Mukhopadhyay et al. ... 382/243 |
| 2004/0062341 A1 | 4/2004 | Popescu et al. |
| 2004/0120564 A1 * | 6/2004 | Gines ............................ 382/131 |
| 2004/0122968 A1 | 6/2004 | Schilling et al. |
| 2005/0002547 A1 * | 1/2005 | Torre-Bueno ................. 382/128 |
| 2005/0033882 A1 | 2/2005 | Peyerl et al. |
| 2006/0291731 A1 * | 12/2006 | Schoisswohl ................. 382/238 |
| 2007/0009080 A1 | 1/2007 | Mistretta |
| 2007/0065032 A1 | 3/2007 | Hernandez et al. |
| 2007/0065033 A1 | 3/2007 | Hernandez et al. |
| 2007/0242798 A1 | 10/2007 | Popescu |
| 2008/0075213 A1 | 3/2008 | Popescu |
| 2008/0205446 A1 | 8/2008 | Popescu et al. |
| 2008/0292168 A1 | 11/2008 | Winkelmann |
| 2009/0046913 A1 | 2/2009 | Chandra |
| 2009/0147908 A1 * | 6/2009 | Garms .............................. 378/4 |

FOREIGN PATENT DOCUMENTS

| | | |
|---|---|---|
| JP | 01093864 | 4/1989 |
| JP | H4-261650 | 9/1992 |
| JP | 06030924 | 2/1994 |
| JP | 07000386 | 1/1995 |
| JP | 08084725 | 4/1996 |
| JP | 10127616 | 5/1998 |
| JP | 2003290216 | 10/2003 |
| WO | 2007038187 A2 | 4/2007 |
| WO | WO-2008155200 | 12/2008 |

OTHER PUBLICATIONS

Manduca, Armando et al., "Histogram transformation for improved compression of CT images," SPIE vol. 3031 (1997) 320-327.

Thammineni, Arunoday, et al., "Segmentation-based CT Image Compression," SPIE Vo. 5371 (2004) 160-169.

Wegener, U.S. Appl. No. 12/208,839 entitled "Adaptive Compression of Computed Tomography Projection Data," filed Sep. 11, 2008, 36 pages.

Wegener, U.S. Appl. No. 11/949,670 entitled "Compression and Decompression of Computed Tomography Data," filed Dec. 3, 2007, 28 pages.

Wegener, U.S. Appl. No. 12/352,116, filed Jan. 12, 2009 entitled "Compression and Storage of Projection Data in a Computed Tomography System," 73 pages.

Wegener, U.S. Appl. No. 12/352,322, filed Jan. 12, 2009 entitled "Compression and Storage of Projection Data in a Rotatable Part of a Computed Tomography System," 71 pages.

Search Report Mailed Apr. 14, 2010 in PCT/US2009/056475 10 pages.

Bae, Kyongtae T., et al., "CT Data Storage Reduction by Means of Compressing Projection Data Instead of Images: Feasibility Study," Radiology, vol. 219, No. 3, Jun. 2001, 850-855.

Search Report and Written Opinion from PCT/US2008/085417 mailed Jun. 2, 2008, 11 pages.

Search Report Mailed Jun. 2, 2009 in PCT/US2008/085417 11 pages.

Search Report Mailed Mar. 30, 2010 in PCT/US2009/056469 10 pages.

Young, Susan S., et al., "Statistically lossless image compression for CR and DR," SPIE Vo. 3658, Feb. 1999, 406-419.

* cited by examiner $$A = \begin{bmatrix} a11 & a12 & a13 & a14 & \bullet & \bullet & \bullet \\ a21 & a22 & a23 & a24 & & & \\ a31 & a32 & a33 & a34 & & & \\ \bullet & & & & & & \\ \bullet & & & & & & \\ \bullet & & & & & & \end{bmatrix}$$

$$B = \begin{bmatrix} b11 & b12 & b13 & b14 & \bullet & \bullet & \bullet \\ b21 & b22 & b23 & b24 & & & \\ b31 & b32 & b33 & b34 & & & \\ \bullet & & & & & & \\ \bullet & & & & & & \\ \bullet & & & & & & \end{bmatrix}$$

Figure 5

EDGE DETECTION FOR COMPUTED TOMOGRAPHY PROJECTION DATA COMPRESSION

BACKGROUND OF THE INVENTION

The present invention relates to compression and decompression of projection data acquired for computed tomography (CT), particularly to determining boundaries using derivatives and compressing the data between the boundaries.

In a CT imaging systems, multiple x-ray radiographic views of an object produce sets of projection data. Each line of projection data represents an integration of density values of internal structures within a plane, or slice, of the object. From the multiple sets of projection data, the CT imaging system produces two-dimensional (2D) cross-sectional images and three-dimensional (3D) images of the internal structures of the object. The images are obtained through application well-known image reconstruction algorithms to the sets of projection data. The techniques that reconstruct cross-sectional images or three-dimensional images from multiple sets of projection data are broadly referred to as "tomography". Performing the image reconstruction using a programmable processor-based device is broadly referred to as computed (computerized or computer-assisted) tomography. In a typical application, a source of x-ray radiation projects x-rays through an object onto an x-ray sensor (or detector) array. The x-ray sensor outputs are digitized to form a set of projection data. The set of projection data can be one-dimensional or two-dimensional depending on the geometry of the detector array. Relative movement between one or more of the object, the x-ray source and the x-ray sensor array provides multiple views having different perspectives. An image of a slice through the object, or a cross-sectional image, can be approximated by the use of mathematical transforms of the multiple views. In certain applications, the cross-sectional images may be combined to form a 3D image of the object that may be otherwise unobservable.

A well-known application of x-ray CT is in medical CT scanners for non-invasive imaging of a human body. In medical CT scanners, multiple views are obtained by rotating the x-ray source and detector array using a gantry and transferring the projection data across the slip ring. Modern CT scanners (as of 2008) digitize tens of thousands of x-ray sensor outputs in the range of one to ten kilosamples per second (ksamp/sec) with each digital sample having 16 to 24 bits per sample, resulting in an aggregate data transfer bandwidth of many gigabits per second (Gbps) across the slip ring. The projection data must also be stored or buffered in real time prior to image reconstruction. The image reconstruction process is typically 10 to 20 times slower than the data acquisition process, creating the need for storage. Typical storage subsystems include redundant arrays of independent disk (RAID) drives. As data transfer rates across the slip ring increase, the storage capacity and throughput of the RAID subsystem must also increase. As the industry strives for increased spatial and temporal resolution and increased numbers of x-ray sensors, the bandwidth demand for data transfer and data storage subsystems will soon surpass 10 Gbps.

Another application of x-ray CT is in automated inspection of industrial products. For example, cross-sectional images reconstructed from x-ray projection data is used in quality control inspection systems for manufactured products including as electronic devices, such as printed circuit boards. Tomography can be used to reconstruct images of one or more planes, or cross-sections, of an object under study in order to evaluate the quality of the object. The x-ray CT system acquires sets of projection data at various location and views with respect to the object of interest. The system architectures for industrial inspection systems differ from medical CT scanners. However, like medical CT systems, large volumes of projection data require data transfer and storage. For automated inspection systems, higher throughput of the objects under test is desirable because it reduces the cost of the product being tested. A higher throughput increases the bandwidth demands for data transfer and data storage. Another example of automated inspection using CT scanning techniques is automatic baggage screening systems.

The large volumes of projection data acquired by a data acquisition subsystem of a CT system create a burden on system resources for data transfer and data storage. Limitations in data transfer bandwidth delays the availability of projection data for the reconstruction and display of an image of the object being scanned. Compressing the projection data prior to data transfer followed by decompression before image reconstruction processing reduces the burden on system resources for data transfer and storage. The benefits of compression include reducing latency between data acquisition and image display, increasing the volume of data transferred over a communication channel having limited bandwidth, and providing compressed projection data for storage and transmission over a network for later access and image reconstruction. Since compression allows the system resources to accommodate more projection data, the image resolution can be improved and/or a larger region of the object can be scanned. The availability of computing resources to implement compression operations is also a constraint in CT systems. It is desirable that the compression operations have low computational complexity and can operate in real time to minimize the impact on computing resources.

In computed tomography, there are two domains of image-related data, the Radon transform domain and the spatial domain. The projection data, or sinogram data, are in the Radon transform domain, also referred to as the projection domain or sinogram domain. The projection data can be 2D in the situation where projection data are obtained for one slice of the object or resulting from a linear array of x-ray sensors. The projection data can be 3D in the situation where projection data are obtained for more than one slice of the object or resulting from a two-dimensional array of x-ray sensors. The 2D cross-sectional images reconstructed from the projection data are in the 2D spatial domain. A three-dimensional image reconstructed from the multiple cross-sectional images is in the 3D spatial domain. The Radon transform is the mathematical transform that underlies the relationship between the projection data in the Radon transform domain and the spatial domain image reconstructed from the projection data. Applying a compression algorithm to the projection data in the Radon transform domain will not produce the same results as applying the same algorithm to the reconstructed image in the spatial domain because of the mathematical relationship between the projection data and the reconstructed image.

Image compression techniques, for example JPEG image compression, are typically applied to spatial domain image data, for example photographic images. Spatial domain image compression techniques are also applied to reconstructed images in computed tomography for efficient image storage or transmission of the spatial domain image. An approach to achieve additional compression in the spatial domain image is to identify regions of interest in the image and apply lossless compression to the regions of interest and lossy compression to areas outside the region of interest. Examples of this approach are described in the article entitled, "Segmentation-based CT Image Compression" by Thammineni et al. in the Proceedings of SPIE, Vol. 5371, pp. 160-169, 2004, and in the conference paper entitled, "CT Image compression with Level of Interest," by Hashimoto et al., IEEE 2004 International Conference on Image Processing, pp. 3185-88.

For the projection, or sinogram, domain, compression and decompression of projection data are applied prior to reconstruction of an image in the spatial domain. Some approaches to compression of projection data apply a JPEG image compression method in the projection domain. An example of this approach is described by Bae et al. in U.S. Pat. No. 7,327,866 entitled, "Method and Apparatus for Compressing Computed Tomography Raw Projection Data," issued Feb. 5, 2008. This approach applies lossless or lossy compression to the projection data. An approach to compress the projection data that falls within the boundaries of object being scanned is described by Nishide et al. in the Japanese published patent application entitled, "X-Ray CT Apparatus, System and Projection Data Compressing/Restoring Method", Kokai (unexamined) Patent Publication Number 2003-290216 (P2003-290216A), published on Oct. 14, 2003. This approach separates the projection data into air information regions, where the x-rays have traversed an empty region, and subject information regions, where the x-rays have traversed the object or patient. Different compression methods are applied to the air information region and the subject information region or the air information region may be deleted.

Disadvantages of the above approaches to compression of the projection data include the following. The bit rate of the compressed data can vary unpredictably in the above techniques because the regions of interest defined and lossless compression are data dependent. Since the bandwidth of the compressed data varies over time, an interface such as a FIFO is required to support the varying data rates. A FIFO interface is more complicated than a fixed-rate interface, since it requires additional control signals (half full, almost full, almost empty, etc.). It would be advantageous to achieve a compressed data the bit rate that falls within a desired range. A lossy fixed-rate compression mode allows control of the bandwidth of compressed data. The compressed data can then be transferred across an interface to a storage medium at a fixed data rate. The fixed data rate simplifies the interface for transfer of the compressed data and minimizes the FIFO depth. Another disadvantage of the above approaches is computational complexity, depending on which compression method is applied. It would be advantageous to reduce the computational complexity to decrease the burden on system resources and allow real time compression of the projection data.

The commonly owned and co-pending U.S. patent application Ser. No. 11/949,670 (the '670 application), entitled "Compression and Decompression of Computed Tomography Data", filed on Dec. 3, 2007, describes compressing projection data and decompressing the compressed projection data prior to image reconstruction. The '670 application teaches classifying the projection data samples into subsets based on their significance. The compression operations applied to the subsets depend on the significance of the projection data samples.

In this discussion, "real time" means a rate that is at least as fast as the sample rate of a digital signal. The term "real time" can be used to describe rates for processing, transfer and storage of the digital signal. The sample rate is the rate at which an analog to digital converter (ADC) forms samples of a digital signal during conversion of an analog signal. When converting a digital signal to an analog signal, the sample rate is the rate at which the digital to analog converter (DAC) forms the analog signal from the samples of the digital signal. The bit rate of an uncompressed sampled, or digital, signal is the number of bits per sample multiplied by the sample rate. The compression ratio is the ratio of the bit rate of the original signal samples to the bit rate of the compressed samples. For this application, real time refers to the rate at which the ADC forms the digital samples of projection data from the output signal of the x-ray sensor.

This description refers to lossless and lossy compression. In lossless compression, the decompressed samples have identical values to the original samples. If lossless compression does not give adequate reductions in the bit rate of the compressed samples, then lossy compression may be necessary to provide sufficient reduction of the bit rate. In lossy compression, the decompressed samples are similar, but not identical to, the original samples. Lossy compression creates a tradeoff between the bit rate of the compressed samples and the distortion in the decompressed samples.

SUMMARY OF THE INVENTION

Embodiments of the present invention have been made in consideration of the foregoing conventional problems. An object of the present invention is to compress CT projection data. The benefits of compressing CT projection data include increasing the efficiency of data transfer across the slip ring interface of a CT scanner, reducing the bandwidth of data delivered to a storage subsystem such as a RAID array and reducing the storage capacity required for a set of projection data in a CT imaging system. A further object of the present invention is to provide a fixed output bit rate. User-specified control of the output bit rate, or bits per sample, of the compressed data results in predictable data transfer rates and data storage requirements. Additional cost savings for CT system components can be achieved when the user-specified compression ratio is an integer value, such as 2:1. For example, a fixed 2:1 compression ratio allows some components of the system such as memory, field programmable gate arrays (FPGA), cables for data transfer and disk drives for data storage to be reduced by half.

To realize the foregoing objects, one aspect of the present invention provides a method for compressing projection data in a computed tomography system that includes a plurality of sensors providing a plurality of sensor measurements to form one or more sets of projection data, wherein each set includes an array of samples of the projection data, the array having at least one line of samples, wherein each sample has a position in the array indicated by a sample coordinate. The method comprises:

detecting a first edge sample and a second edge sample in the line of the array;

determining a first boundary based on the first edge sample and a second boundary based on the second edge sample;

compressing samples having sample coordinates between the first boundary and the second boundary to form compressed samples; and encoding the respective boundaries to form encoded boundaries included with the compressed samples, wherein the step of detecting comprises:

calculating differences between consecutive samples in the line of the array to form difference samples, each difference sample having a positive value or a negative value; and comparing the positive difference samples to a positive threshold and the negative difference samples to a negative threshold to determine the first edge sample and the second edge sample.

Another aspect of the present invention provides an apparatus for compressing projection data in a computed tomography system that includes a plurality of sensors providing a plurality of sensor measurements to form one or more sets of projection data, wherein each set of projection data represents a portion of a projection domain and includes an array of samples of the projection data, the array having at least one line of samples, wherein each sample has a position in the array indicated by a sample coordinate. The apparatus comprises:
- a compression subsystem coupled to receive the samples of the projection data and providing compressed samples to a data transfer interface, the compression subsystem further comprising:
- an edge detector applied to samples in the line of the array, wherein the edge detector determines a first edge sample and a second edge sample in the line of samples and sets a first boundary and a second boundary based on the first edge sample and the second edge sample, respectively;
- a compressor that compresses the samples corresponding to the sample coordinates between the first boundary and the second boundary to form the compressed samples; and
- a boundary encoder that encodes the first and second boundaries to include with the compressed samples, wherein the edge detector further comprises:
- a difference calculator that calculates a plurality of differences between samples in the line of the array to form difference samples, each difference sample having a positive value or a negative value; and
- a threshold operator applied to the positive difference samples and the negative difference samples to produce the first edge sample and the second edge sample.

BRIEF DESCRIPTION OF THE DRAWINGS

FIG. 5 illustrates an example of two arrays of attenuated samples corresponding to different sets of projection data.

DETAILED DESCRIPTION

The present invention is directed to compression and decompression of projection data in the Radon transform domain, also known as the projection domain or sinogram domain. Compression of projection data allows more efficient data transfer from the data acquisition subsystem of a CT system to a storage subsystem and an image reconstruction processor. Later decompression of the compressed projection data is applied prior to image reconstruction of a spatial domain image. Compression and decompression can be applied to one set of projection data resulting from one view or to multiple sets of projection data resulting from multiple views. The present invention is independent of the number of views used by the image reconstruction processor to compute a spatial domain image.

Embodiments of the present invention can be used for compressing and decompressing projection data in a medical computerized tomography scanner for generating cross-sectional images of a human body and in industrial computed tomography systems for inspecting an object under study. In medical computerized tomography scanners, an x-ray source and detector array are rotated about the patient by a rotating gantry. The projection data acquired by the detector array are transmitted via a communication channel between the rotating unit and the stationary unit of the gantry system to a storage system and later to a processor for image reconstruction. In an industrial computed tomography system, the x-ray source and detector array may have limited motion or remain stationary and the object under study may be translated or rotated. The projection data are transmitted by a communication link to a storage device and later to a processor for image reconstruction. In both applications, the communication channels each have limited bandwidth. The bandwidth limitation determines the speed of transmission of the projection data to the processor for use in image reconstruction. The projection data are compressed prior to transmission so that more data can be transferred across the limited bandwidth channels. In applications where the projection data are stored, compression of the projection data allows more data to be stored in a given memory capacity or reduces the required memory capacity and memory interface bandwidth. The compressed projection data are decompressed and processed for image reconstruction.

Figure 1A:
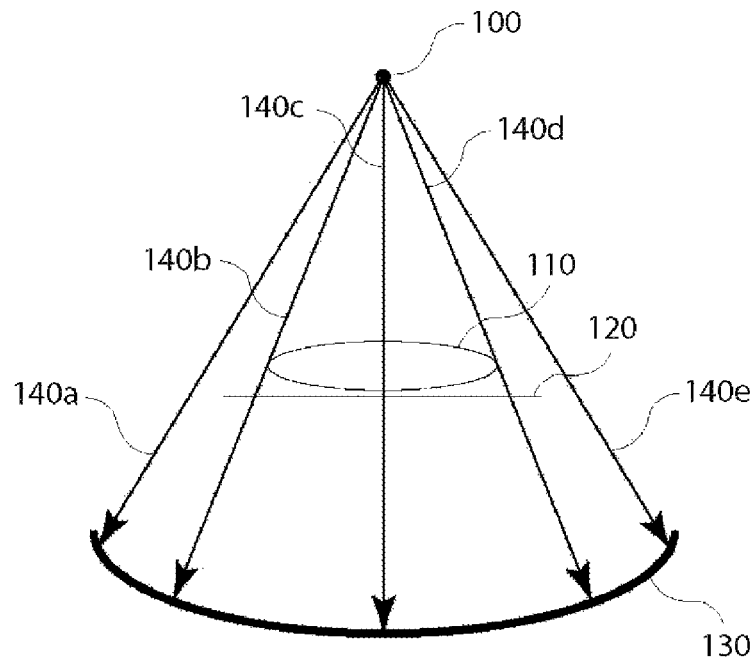
FIG. 1a is an illustration representing the basic configuration for CT scan data acquisition in a medical CT imaging system, in accordance with the prior art.

FIG. 1a is an illustration representing the basic configuration for CT scan data acquisition in a medical CT imaging system. An object or patient 110 is positioned on a platform 120 that can be moved back and forth within a rotating gantry (not shown) of a CT imaging system. The gantry includes an x-ray source 100 and a data acquisition subsystem (DAS) 130. The DAS 130 includes a matrix of one or more rows of x-ray sensors and analog to digital converters (ADCs). The ADCs digitize signals from the x-ray sensors to produce samples whose amplitudes represent x-ray counts or Hounsfield units. A present (2008) CT system can include a matrix of approximately 1024 x-ray sensors per slice, or row, and up to 320 slices per view. The x-ray source 100 generates a beam having a particular geometry, depending on the system design. The example shown in FIG. 1a has fan-beam geometry. The degree of attenuation of the x-ray depends on its path. In FIG. 1a, the rays 140a and 140e are unattenuated because they travel through the air. The ray 140c is attenuated because it is partially absorbed when traversing the object 110. The rays 140b and 140d traverse boundaries of the object 110, so they will be less attenuated than ray 140c. The array of x-ray sensors measures the received x-rays to form signals for the ADCs. The x-ray sensors of CT scanners require a dynamic range of many orders of magnitude to capture the range of attenuated and unattenuated x-ray signals from the x-ray source 100. The x-ray sensors of current (2008) CT scanners use ADCs that sample the x-ray sensor output using 16 to 24 bits per sample. For 16 bits per sample, the maximum (unattenuated) x-ray count is $2^{16}$, or 65,536. For 24 bits per sample the maximum x-ray count is $2^{24}$, or 16,777,216. For each view angle increment, the DAS 130 produces a set of projection data. The set of projection data includes an array of samples, where a line of samples in the array, or scan line, corresponds to the measurement of x-rays passing through a slice of the object 110. As the gantry rotates around the patient, multiple sets of projection data are captured and transferred across the slip ring to an external computer or processor (not shown in FIG. 1a). The processor applies an image reconstruction algorithm to the sets of projection data to form an image. The image reconstruction algorithm can produce two-dimensional cross-sectional images or three-dimensional images of the scanned object, depending on the scan protocol. The reconstructed image is then displayed for analysis. The particular geometry of the x-ray source beam, the detector geometry, DAS 130 configuration or scan protocol do not limit applications of the present invention.

Figure 1B:
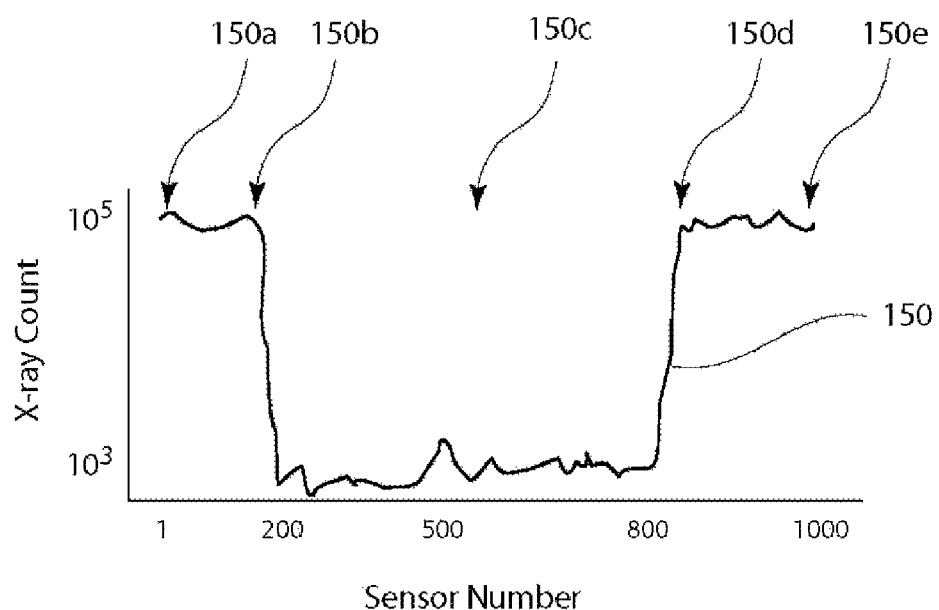
FIG. 1b illustrates an example of a signal formed by projection data output from a row of sensors, in accordance with the prior art.

FIG. 1b illustrates an example of a signal 150 formed by projection data output from a row of sensors of DAS 130. The regions 150a and 150e correspond to the unattenuated rays 140a and 140e and have the maximum x-ray counts. The regions indicated by 150b and 150d are transitional regions representing the rays detected at the boundaries 140b and 140d. The region indicated by 150c corresponds to attenuated ray 140c that has traversed the object 110 and thus has a substantially lower x-ray count. The CT systems in use typically include a matrix of sensors that is wider than the objects that are scanned, so regions with unattenuated x-rays, such as regions 150a and 150e commonly occur in projection data. In the reconstructed image, these "empty" regions correspond to regions outside the reconstructed image. The CT image reconstruction algorithms typically do not use the projection data from the empty regions 150a and 150e.

For the example of FIG. 1b, the projection data corresponding to empty space have higher values than projection data corresponding to rays traversing the object. In some CT systems, preprocessing produces projection data where samples corresponding to empty space have lower values than samples corresponding to the object. For this description, it is assumed that the indices of the samples increase from left to right. However, conventions for representing the sample coordinates do not limit the scope of the present invention.

Figure 2:
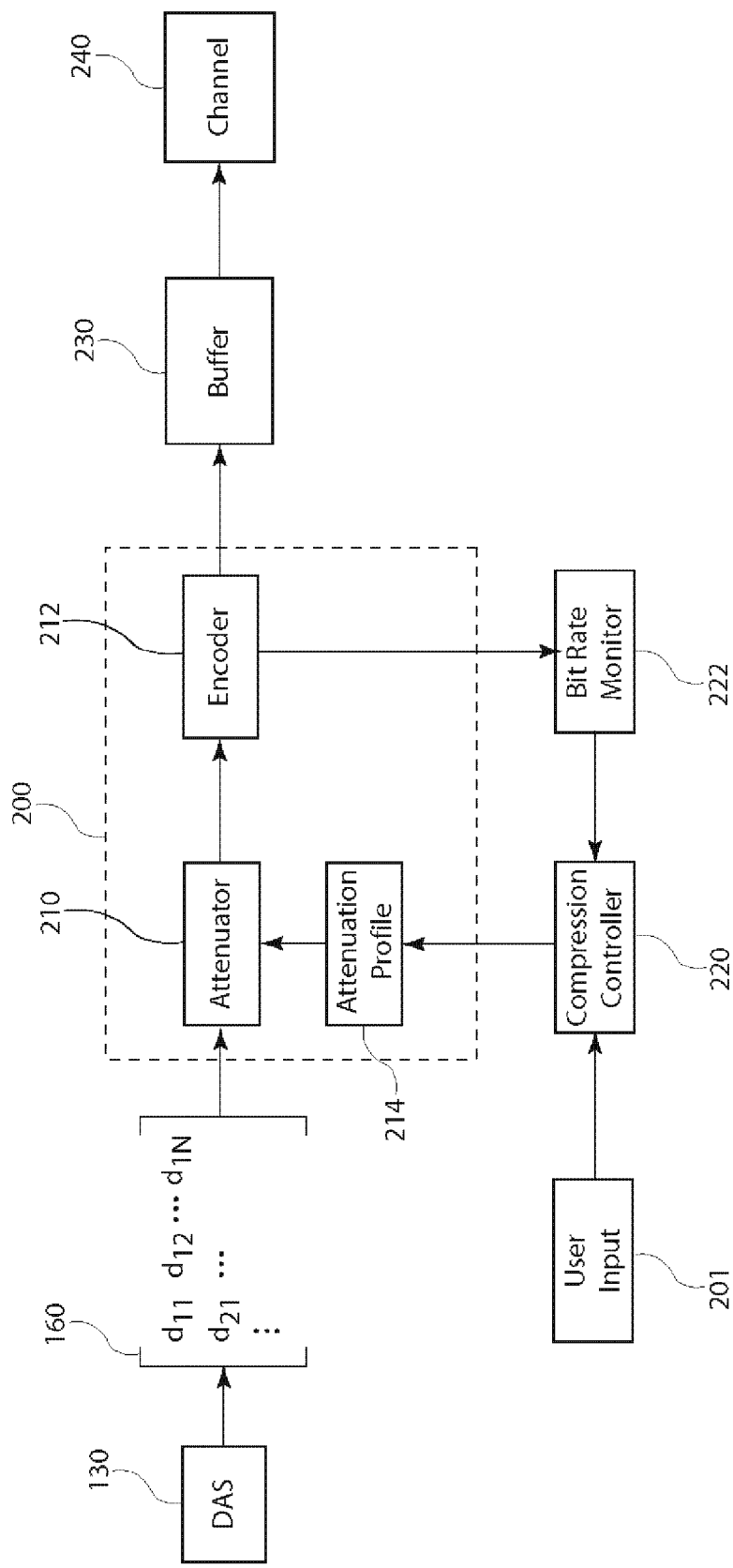
FIG. 2 is a block diagram of a compression system for projection data, in accordance with a preferred embodiment.

FIG. 2 is a block diagram of a compression system for projection data. The DAS 130 generates a set of projection data 160 for each view. The set of projection data 160 comprises an array of projection data samples. The array geometry depends on the data acquisition process and does not limit the scope of the present invention. The array of projection data 160 includes projection data samples $d_{11}$, $d_{12}$, etc., having associated coordinates, or indices. The compression processor 200 compresses the projection data samples of the array 160. The attenuator 210 reduces the magnitudes of the samples in each line, or row, of the array 160 in accordance with parameters of the attenuation profile 214. The attenuation profile 214 depends on the coordinates of the samples in the array 160 and provides attenuation values that are less than or equal to one. The magnitude of an attenuated sample is either reduced or remains at the original value, depending on the attenuation profile 214. The attenuator 210 essentially reduces the dynamic range of the attenuated samples so that they can be represented using fewer bits. The encoder 212 packs the attenuated samples using lossless or lossy encoding, as described further below. The encoder 212 outputs the compressed samples to a buffer 230 for transmission via a communication channel 240. In a CT scanner system, the slip ring interface provides the communication channel 240. The compression controller 220 receives feedback information from the encoder 212. The feedback information can include compressed data bit rate or number of bits per compressed sample. The compression controller 220 uses feedback information to adjust the compression control parameters, including parameters of the attenuation profile 214, so that the compressed data bit rate, or number of bits per compressed sample, remains constant or falls within a desired range. The compression control parameters, including parameters corresponding to the attenuation profile 214, can be encoded and included with the compressed data and later used for decompression control. The compression controller 220 can also receive user input 201, such as a desired output bit rate for compressed data, selection of compression operations and setting control parameters.

The attenuation profile 214 includes parameters that determine the degree of attenuation applied by the attenuator 210 to the samples in the array 160. A preferred type of attenuation profile 214 is represented by a function having segments that are exponential functions of base 2. In one alternative, the attenuation profile 214 provides decreasing attenuation from the boundaries of each line of the array 160 towards the center. For example, assume that the coordinates for the $i^{th}$ line, or row, in the array 160 $d_{ij}$ extends from $j=1$ to $j=N$, where N represents the number of X-ray sensors in a row of DAS 130. For example, in a current (2008) CT system, the array can have lines with up to 1024 elements per line, or row. An exponential attenuation profile provides attenuation as a function $g(j)$ of the sample coordinate $j$, given by:

$$g(j)=2^{-y(j)} y(j) \geq 0 \quad (1)$$

The attenuation profile 214 represented by $g(j)$ includes an exponent function $y(j)$. Since the exponent is negative in equation (1), multiplying the samples by the values of the function $g(j)$ reduces the magnitudes of the samples, unless $y(j)=0$. The exponent function $y(j)$ is the negative $\log_2$ of the attenuation profile represented by $g(j)$. The number of bits (including fraction of a bit) needed to represent the $j^{th}$ attenuated sample is less than that of the $j^{th}$ unattenuated sample by the $j^{th}$ value of the exponent function $y(j)$.

Figure 3A:
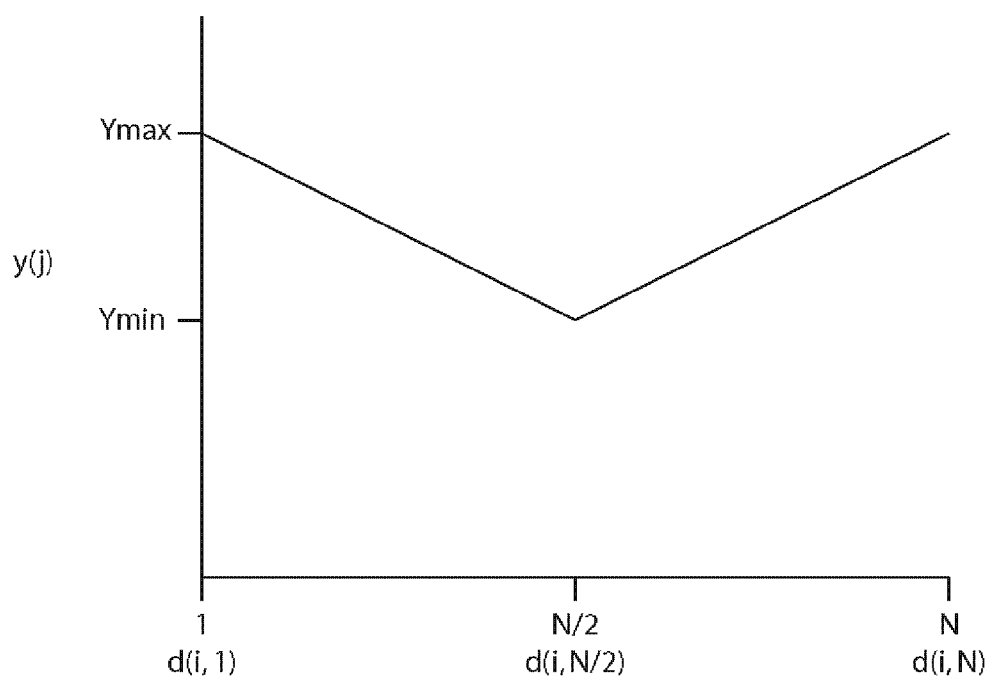
FIG. 3a shows an example of an exponent function y(j) of the attenuation profile given by the function $g(x)=2^{-y(j)}$.

FIG. 3a shows an example where the exponent function $y(j)$ comprises segments that are linear functions of the index $j$. The y-axis indicates the number of bits (including fraction of a bit) of reduction in the magnitude of the $j^{th}$ sample. The parameter Ymax will produce the maximum attenuation, given by:

$$g_{max}=2^{-Ymax} \quad (2)$$

The symmetric exponent function shown in FIG. 3a would apply the maximum attenuation to the samples $d(i,1)$ and $d(i,N)$ in the $i^{th}$ line of the array 160. The value of Ymax is less than or equal to the bit precision of the projection samples produced by the DAS 130 and can be selected to achieve a target output bit rate of the compressed data, as described below with respect to FIG. 7. For example, when 20 bit samples are produced by the DAS 130, the value of Ymax is 20 or less. A lower value of Ymax, such as 10 for the 20 bit samples, produces lower attenuation resulting in less compression. The parameter Ymin corresponds to the minimum attenuation, given by $$g_{min}=2^{-Ymin} \quad (3)$$

Figure 3B:
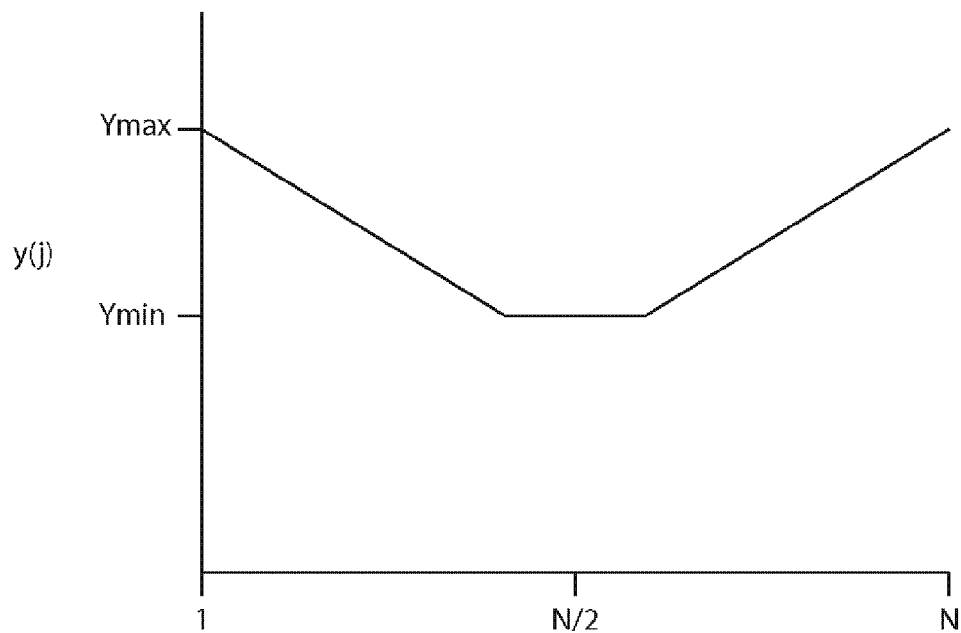
FIG. 3b shows another example of an exponent function y(j) of the attenuation profile given by the function $g(x)=2^{-y(j)}$.

For Ymin=0, the center sample corresponding to $d(i,N/2)$ in FIG. 3a would remain at the same magnitude. The value of Ymin can also be adjusted to achieve a target output bit rate, as described below with respect to FIG. 7. Another example for the exponent function includes multiple linear segments, as shown in FIG. 3b. Alternatively, the exponent function can have segments that are nonlinear functions of the sample coordinates.

The attenuation profile can be represented by linear, exponential, parabolic, staircase, dithered or other nonlinear segments. Also, the attenuation profile need not be symmetric or have its minimum value at the center (N/2) element of the N-length line of array 160. Preferably, the attenuation profile provides gradual changes from sample to sample. It has been observed that a change in the attenuation profile between samples that is greater than one bit can cause ring artifacts in the reconstructed image. For some non-medical CT applications, the ring artifacts may be tolerable. For medical CT, the ring artifacts can be prevented. To prevent the ring artifacts, an attenuation profile represented by g(j) should change by less than one bit per sample index j. This constraint is also represented as follows:

$$\text{Abs}[\log_2(g(j)) - \log_2(g(j+1))] < 1$$

For g(j) represented in equation (1), the magnitudes of the slopes of the line segments for y(j) must be less than or equal to one to meet this constraint. The examples of FIGS. 3a and 3b meet this constraint. This constraint can also be expressed using units of decibels (dB). One bit represents 6 dB of attenuation, so an attenuation step of less than 6 dB per sample index meets the above criteria. For example, an attenuation step of 0.375 dB corresponds to $\frac{1}{16}$ bit, and it has been observed that ring artifacts apparent with attenuation steps of 6 dB are not present when the attenuation step is reduced to 0.375 dB. Accordingly, the critical attenuation step will depend on the application of the CT imaging. In high resolution CT systems, a critical attenuation step to avoid ring artifacts can be less than 1 dB. The magnitude of the attenuation step is inversely related to the compression ratio that can be achieved. Therefore, for systems requiring a compression ratio of at least 2 to 1, higher attenuation steps are suggested. It is discovered that significant compression is achievable using the attenuation and encoding technology described herein, while maintaining a smoothly reconstructed image in high resolution CT systems for medical imaging.

It is preferred that the attenuation profile apply greater attenuation to samples near the edges of the array 160 and lower or no attenuation to samples near the center of the array in order to preserve the accuracy of the central area of the reconstructed image. When the attenuation of the samples results in lossy compression, the accuracy of the central area of the reconstructed image is preserved, while the error is increased in the peripheral area. The attenuation profile can be represented by functions having linear, exponential, parabolic or other nonlinear segments. The attenuation profile values may be the same for all the lines of the array. Alternatively, the attenuation profile values may vary for the different lines of the array or for the different projection data sets.

The attenuator 210 applies the attenuation profile 214, such as that represented by equation (1), by multiplying and/or shifting the samples by the corresponding attenuation values. Multiplying along with shifting allows fractional attenuation values in the floating point range {0.0, 1.0}. For example, representing the floating point attenuation values of the attenuation profile using M bits provides $2^M$ attenuation values in the range {0.0, 1.0}. The attenuation values themselves can be stored in a lookup table in memory and provided to the attenuator 210. Alternatively, the attenuator 210 can calculate the attenuation values using parameters defining the attenuation profile 214, such as slopes and segment endpoints, stored in memory. A simple embodiment of the attenuator 210 includes right shifting the samples by the number of bits corresponding to the attenuation values. Shifting alone reduces the magnitudes of the samples by factors of 2, since a right shift corresponds to a division by two. When the attenuation profile 214 corresponds to an exponential function of base 2 as in equation (1), the exponent function y(j) can be truncated or rounded to determine a whole number of right shifts. The right shifts will shift out a corresponding number of least significant bits, thus reducing the number of bits used to represent the sample. The right shift values corresponding to the attenuation values can be stored in a lookup table or calculated by the attenuator 210 based on parameters of the attenuation profile 214.

The encoder 212 further reduces the number of bits representing the attenuated samples to produce the compressed samples. The encoder 212 can apply block floating point encoding, Huffman encoding or other bit packing method. Alternatively, since the number of bits per sample is a known function of sample index (represented by the attenuation profile), attenuated samples can be packed sequentially. For example, for the attenuation profile 214 represented by equation (1), the number of bits for the $j^{th}$ sample is reduced by the rounded or truncated value of y(j) so that the number of bits for each compressed sample is known as a function of the sample index j.

The encoder 212 can apply block floating point encoding. The preferred block floating point encoding divides each line of samples to be encoded into groups of N_GROUP samples and applies the following steps.

For the first group of samples:
1) Determine the exponent (base 2) for the sample with the maximum magnitude, such as by calculating the $\log_2$ of the maximum magnitude in each group of N_GROUP samples. This indicates the number of bits per encoded sample, or n_exp(0).
2) Absolute encode the exponent n_exp(0) of the first group using S bits.
3) Encode the N_GROUP samples using n_exp(0) bits per sample.

For the $i^{th}$ group of N_GROUP samples:
4) Determine the $i^{th}$ exponent (base 2) for the sample with the maximum magnitude, which indicates the number of bits per encoded sample in the $i^{th}$ group, or n_exp(i);
5) Differentially encode the $i^{th}$ exponent by subtracting n_exp(i) from n_exp(i−1) to determine an $i^{th}$ difference value. Encode the $i^{th}$ difference value using a corresponding token, where shorter tokens represent more common difference values and longer tokens represent less common difference values.
6) Encode the $i^{th}$ group of N_GROUP samples using n_exp(i) bits per sample.

For the first group of samples, the exponent n_exp(0) is directly encoded. For example, the exponent n_exp(0) can be encoded as follows, where S is the original number of bits per sample:
  a. 0: n_exp(0)=0 (all 4 sample values are zero)
  b. 1: n_exp(0)=2 (2 bits per sample)
  c. 2: n_exp(0)=3 (3 bits per sample)
  d. etc. until S−1: n_exp(0)=S (S bits per sample)

For the $i^{th}$ group, the exponent n_exp(i) is differentially encoded using a prefix code, where no codeword is the prefix of another codeword. The preferred differential encoding is as follows:
1. Calculate difference: e_diff=n_exp(i)−n_exp(i−1)
2. Encode e_diff as follows:
  a. 0: e_diff=e(i)−e(i−1)
  b. 101: e_diff=+1
  c. 110: e_diff=−1
  d. 1001: e_diff=+2
  e. 1110: e_diff=−2
  f. Etc.

An alternative lossy encoding method provides separate encoding of the mantissas and exponents of the sample values. Encoding the mantissas and exponents separately can provide additional compression and reduce the effects of lossy compression error. In this method, the difference values of the exponents of consecutive samples are calculated to determine exponent difference values. The exponents are slowly varying, so there are relatively few nonzero values separated by strings of zero values. The exponent difference values can be efficiently encoded by representing only the nonzero difference value and their corresponding positions. The position can be represented by the corresponding index value or relative to the position of last nonzero difference value. Encoding of the exponent difference values is lossless, which prevents relatively large errors. Encoding of the mantissas can be lossy. For decoding the exponents, the exponent values are reconstructed by integrating the exponent difference values and decoding the corresponding position locations. When decoding the mantissas, each reconstructed mantissa value is restricted to so that it does not change the value of the corresponding exponent of the decoded sample. For a decoded exponent of n exp, the reconstructed mantissa can have a maximum value of $2^{n\_exp}-1$. This prevents lossy compression error in the mantissa from changing the value of the exponent.

Figure 4:
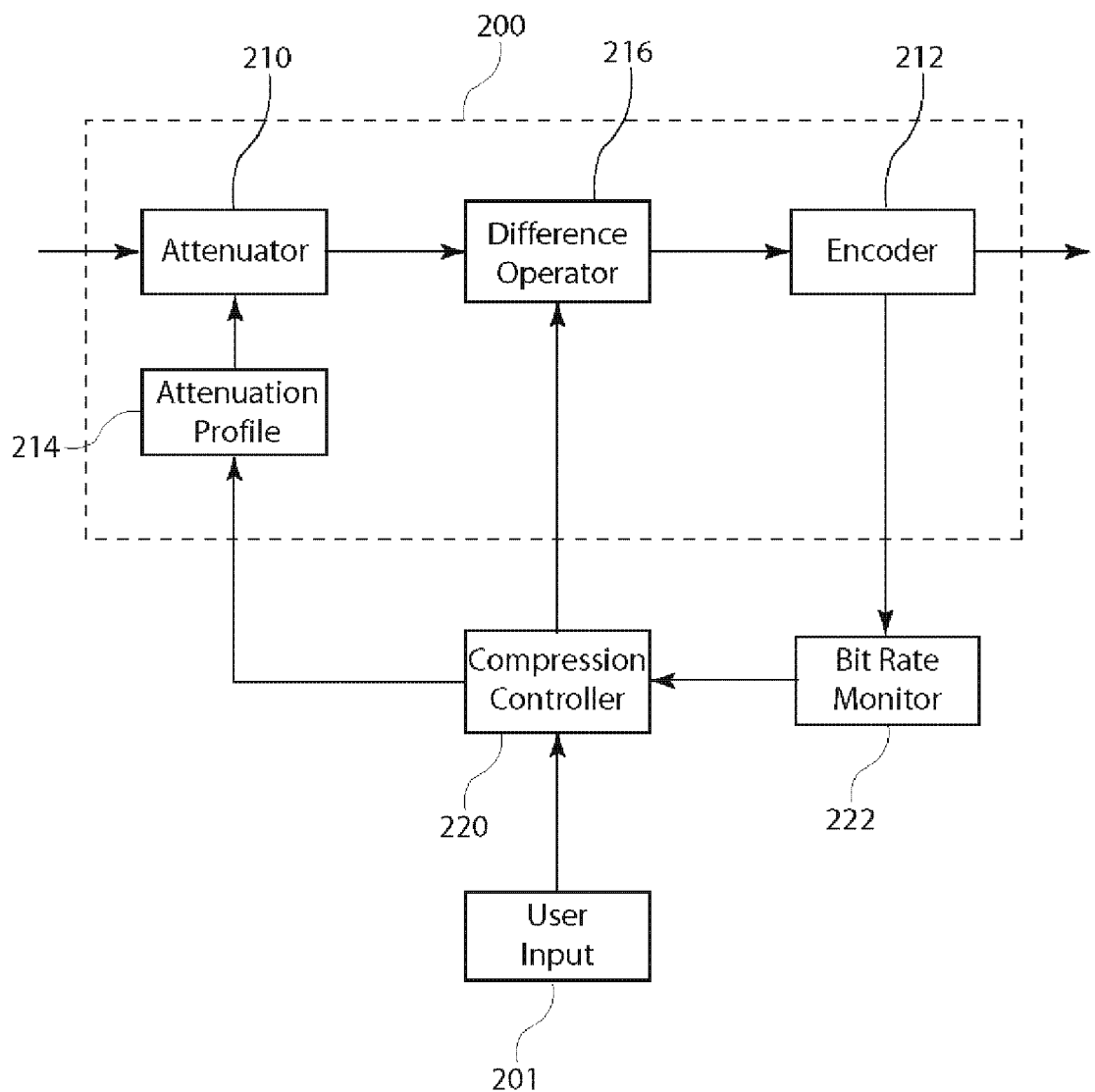
FIG. 4 is a block diagram of a compression system for projection data that includes a difference operator.

Differential encoding of the attenuated samples prior to block floating point or other encoding can provide additional compression. For differential encoding, the compression processor 200 includes a difference operator 216, as shown in FIG. 4. The difference operator 216 calculates first or higher order differences of the attenuated samples. The difference operator 216 has the following alternatives for calculating differences:

1) Calculating differences between consecutive attenuated samples of the same line (row), or column by column differences;
2) Calculating differences between attenuated samples in consecutive lines (rows) of the same set of projection data, or row by row differences;
3) Calculating differences between the attenuated samples in corresponding positions of consecutive sets of projection data, or views.

FIG. 5 illustrates an example of two arrays, A and B, of attenuated samples corresponding to different sets of projection data. For the first alternative the difference operator calculates differences between consecutive samples in the same line, or row. For example for the first row of set 160a, differences calculated between attenuated samples include:

$$\text{Diff3} = a_{14} - a_{13} \quad (4)$$

$$\text{Diff2} = a_{13} - a_{12} \quad (5)$$

$$\text{Diff1} = a_{12} - a_{11} \quad (6)$$

For calculating differences between attenuated samples in different rows of the same set of projection data, an example for array A is as follows:

$$\text{Diff1} = [a_{21}\, a_{22}\, a_{23}\, a_{24}\ldots] - [a_{11}\, a_{12}\, a_{13}\, a_{14}\ldots] \quad (7)$$

$$\text{Diff2} = [a_{31}\, a_{32}\, a_{33}\, a_{34}\ldots] - [a_{21}\, a_{22}\, a_{23}\, a_{24}\ldots] \quad (8)$$

For calculating differences between corresponding attenuated samples of different sets of projection data, an example is as follows:

$$\text{Diff1} = B - A \quad (9)$$

For second order differences, the difference operator 216 calculates the following for the respective examples:

$$S\text{diff1} = \text{Diff2} - \text{Diff1} \quad (10)$$

$$S\text{diff2} = \text{Diff3} - \text{Diff2} \quad (11)$$

For third order differences, the difference operator calculates the following for the respective examples:

$$T\text{diff1} = S\text{diff2} - S\text{diff1} \quad (12)$$

The compression controller 220 provides control parameters that configure the difference operator 216 to perform the desired calculations. The compression controller 220 can respond to user input 201 to set values of the control parameters. The difference values can be quantized to fewer bits for additional bit reduction. The encoder 212 applies block floating point encoding, Huffman encoding or other bit packing method (lossless or lossy), as described above, to the difference samples.

The bit rate monitor 222 in FIGS. 2 and 4 tracks the output bits per sample in the compressed samples for control of the output bit rate. The bit rate monitor 222 calculates the average bits per sample for a group of compressed samples. The average bits per compressed sample is compared to a desired value or range of values. If the average bits per compressed sample is outside the range, the compression controller 220 can adjust parameters of the attenuation profile 214 to reduce or increase the output bits per sample. For example, referring to FIG. 3a, to reduce the output bits per sample, the parameter Ymax can be increased, making the slopes of the line segments steeper to provide increased attenuation of the samples. The bit rate monitor 222 can calculate other measures of compression performance, such as compression ratio.

Figure 6:
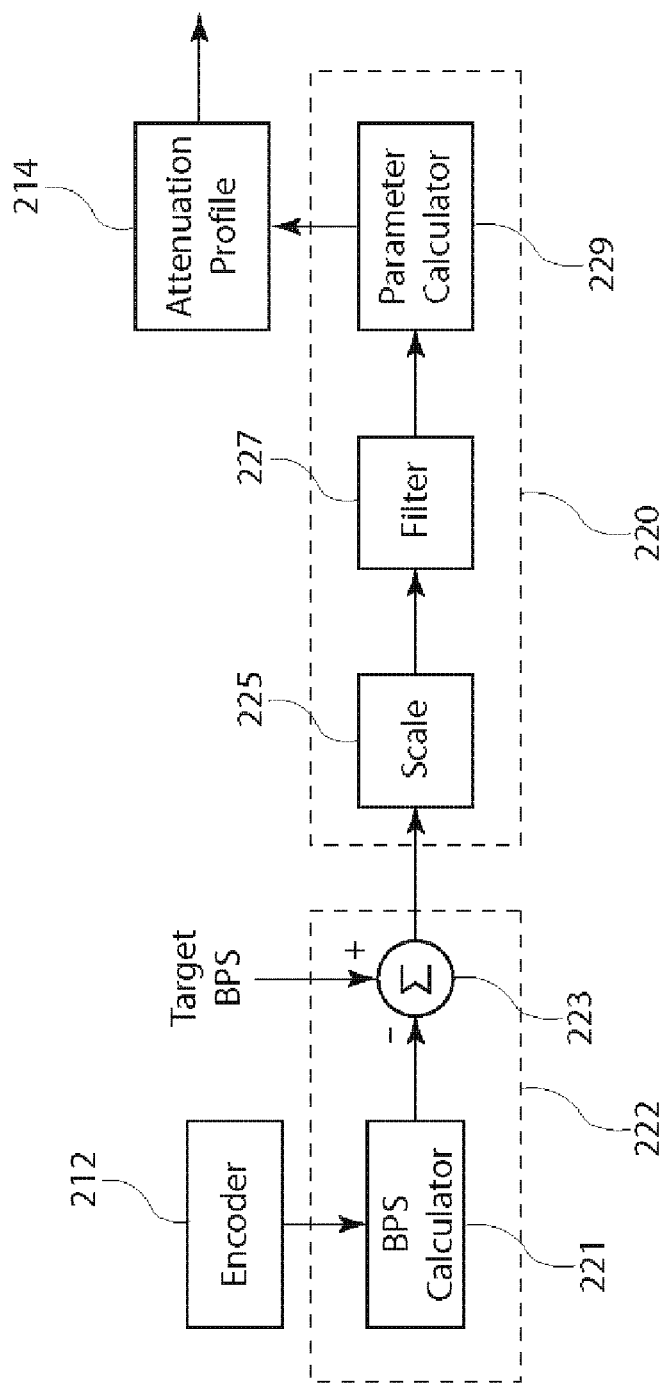
FIG. 6 is a block diagram showing the interactions of the various elements for controlling the average bits per compressed sample.

FIG. 6 is a block diagram showing the interactions of the various elements for controlling the output bit rate to a target value. The bit rate monitor 222 receives compressed bit rate information from the encoder 212, such as compressed bit counts and/or sample counts. The bits per sample calculator 221 calculates the average number of bits per sample for a set of compressed samples. Preferably, the set of compressed samples corresponds to a set of projection data. The subtractor 223 subtracts the average bits per sample from the target, or desired, bits per sample to give an error value. A scale factor 225 and a filter 227 are applied to smooth the error values. The values of the scale factor 225 and filter coefficients can be specified by the user to determine the response time, or time constant, of the feedback loop. The parameter calculator 229 modifies parameters for the attenuation profile 214 based on the smoothed error values. In one approach, the parameter calculator 229 sets the parameters of the attenuation profile 214 so that the mean value of bits reduced per sample approximately equals the smoothed error value. For example, for the attenuation profile 214 represented by equations (1) to (3), the parameter calculator 229 adjusts the values of parameters Ymax and Ymin of the function y(j). Referring to FIG. 3a, the mean value is given by:

$$\text{mean} = (Y\text{max} + Y\text{min})/2 \quad (13)$$

To reduce the bits per sample by an amount r, the parameters Ymax and Ymin can be adjusted so that the new mean value, mean(2), is increased by the amount r from the old mean value, mean(1).

$$\text{mean}(2) = \text{mean}(1) + r \quad (14)$$

$$= [Y\text{max}(1) + Y\text{min}(1) + 2r]/2 \quad (15)$$

Equation 15 shows three alternatives for adjusting Ymax and/or Ymin to increase the mean by an amount r:

1) Set $Y\max(2)=Y\max(1)+2r$ and $Y\min(2)=Y\min(1)$;     (16a)

2) Set $Y\max(2)=Y\max(1)+r$ and $Y\min(2)=Y\min(1)+r$;     (16b)

3) Set $Y\max(2)=Y\max(1)$ and $Y\min(2)=Y\min(1)+2r$;     (16c)

Alternatives 1 and 3 change the slopes of the segments of exponent function y(j). Alternative 2 shifts the exponent function y(j) in the positive direction. The user can determine which of the alternatives is used as a rule for changing the parameters of the exponent function. Other parameters of the attenuation profile 214 and exponent function can be adjusted, such as slopes, y-intercept values and segment lengths.

Figure 7:
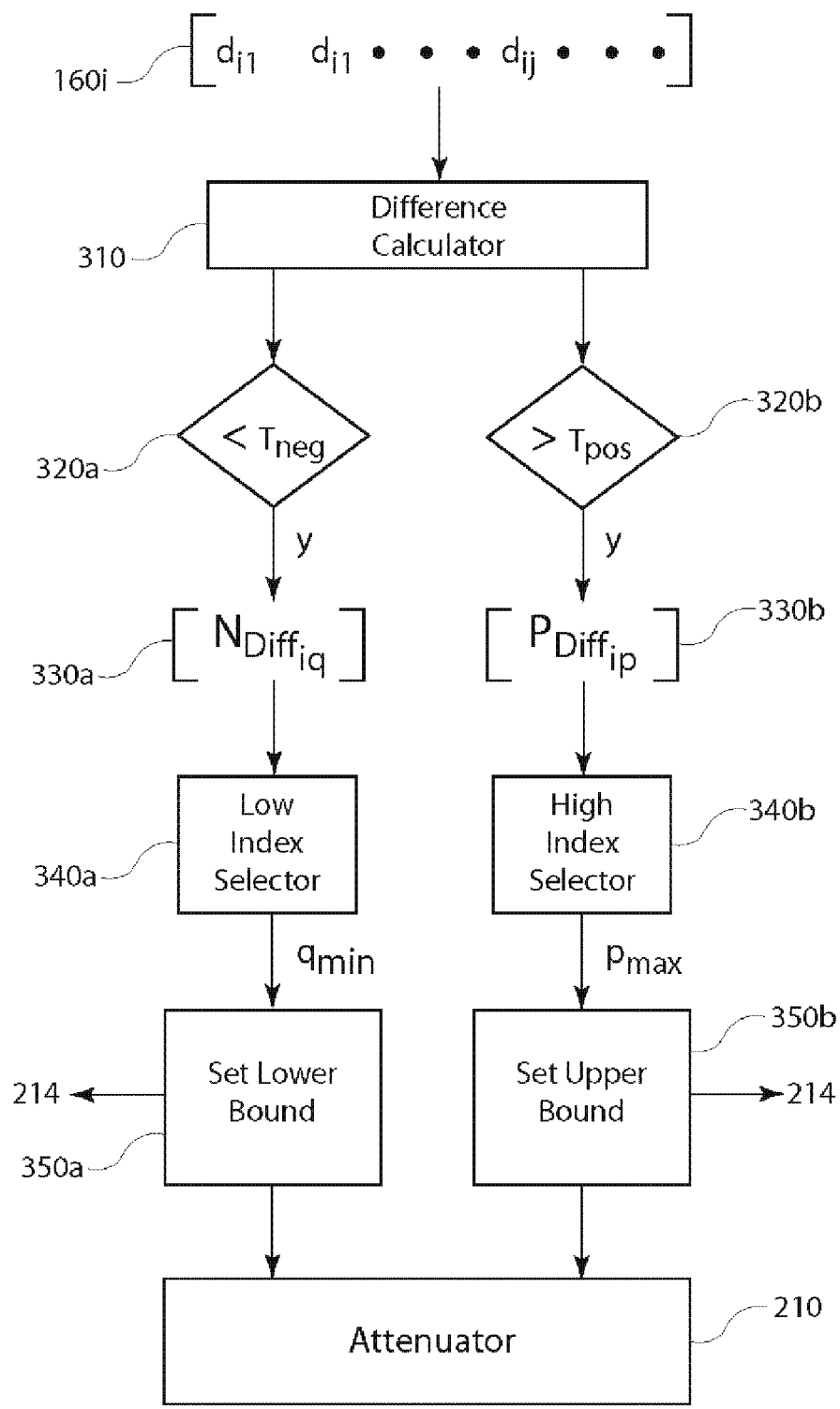
FIG. 7 is a block diagram for the edge detector.

In an alternative embodiment, the attenuation profile 214 can be defined in relation to the boundaries 140b and 140d of the object 110 being scanned in FIG. 1a. An edge detector can determine the edge samples corresponding to the transitions 150b and 150d in each line of the array of projection data 160. The attenuation profile 214 is applied to samples corresponding to attenuated x-rays within the boundaries corresponding to the transitions 150b and 150d. The samples corresponding to empty regions 150a and 150e are not encoded. The coordinates of boundaries are encoded instead. FIG. 7 is a block diagram for an edge detector applied to a line of samples 160i of the array 160. The edge detector block diagram of FIG. 7 applies to projection data where the values of the samples corresponding to empty space 150a and 150e are greater than the values of the samples corresponding to the object 150c, such the signal 150 in FIG. 1b. It is assumed that the indices increase from left to right so that the left edge has a lower valued index and the right edge has a higher valued index. For this situation, a derivative that is negative and sufficiently large can indicate the left edge corresponding to transition 150b and a derivative that is positive and sufficiently large can indicate the right edge corresponding to transition 150d. The difference calculator 310 calculates first order differences of the samples $d_{ij}$ in the $i^{th}$ line. The comparator 320a compares the negative differences to a negative threshold $T_{neg}$ and the comparator 320b compares the positive differences to a positive threshold $T_{pos}$. Negative difference samples less than the negative threshold form candidate samples $NDiff_{iq}$ for set 330a. Positive difference samples greater than the positive threshold form candidate samples $PDiff_{ip}$ for set 330b. The low index selector 340a determines the lowest index $q_{min}$ corresponding to the candidate samples $Ndiff_{iq}$ of set 330a to indicate the left edge. The high index selector 340b determines the highest index $p_{max}$ corresponding to the candidate samples $PDiff_{ip}$ of set 330b to indicate the right edge. The set lower bound block 350a and set upper bound block 350b determine the lower and upper boundaries, respectively, for the attenuation profile 214. The lower and upper boundaries for the attenuation profile 214 may include margins appended to the lowest index $q_{min}$ and highest index $p_{max}$. The lower and upper boundaries are provided as parameters to the attenuation profile 214. The encoder 212 also encodes the lower and upper boundaries to include with the compressed samples.

For the situation where values of the samples corresponding to empty space are less than the values of the samples corresponding to the projection data of an object being imaged, relationship of the positive and negative differences to the right and left edges is reversed. The positive difference samples greater than the positive threshold correspond to the left edge and the negative difference samples less than the negative threshold correspond to the right edge. For the operations shown in FIG. 7, the comparator 320a and set 330a for the negative differences would provide input to the high index selector 340b and the comparator 320b and set 330b would provide input to the low index selector 340a. Again, it is assumed that the indices increase from left to right.

The negative threshold $T_{neg}$ and positive threshold $T_{pos}$ can be determined iteratively as follows:

1) Set initial thresholds $T_{neg}$ and $T_{pos}$ to have maximum magnitudes;
2) Apply comparators 320a and 320b to compare negative differences to $T_{neg}$ and positive differences to $T_{pos}$, respectively;
3) If the set of candidate samples 330a or 330b is empty, reduce the magnitude of $T_{neg}$ or $T_{pos}$, respectively, and reapply step 2);
4) If the set of candidate samples 330a or 330b is not empty, continue with the low index selector 340a or the high index selector 340b, respectively.

Figure 8:
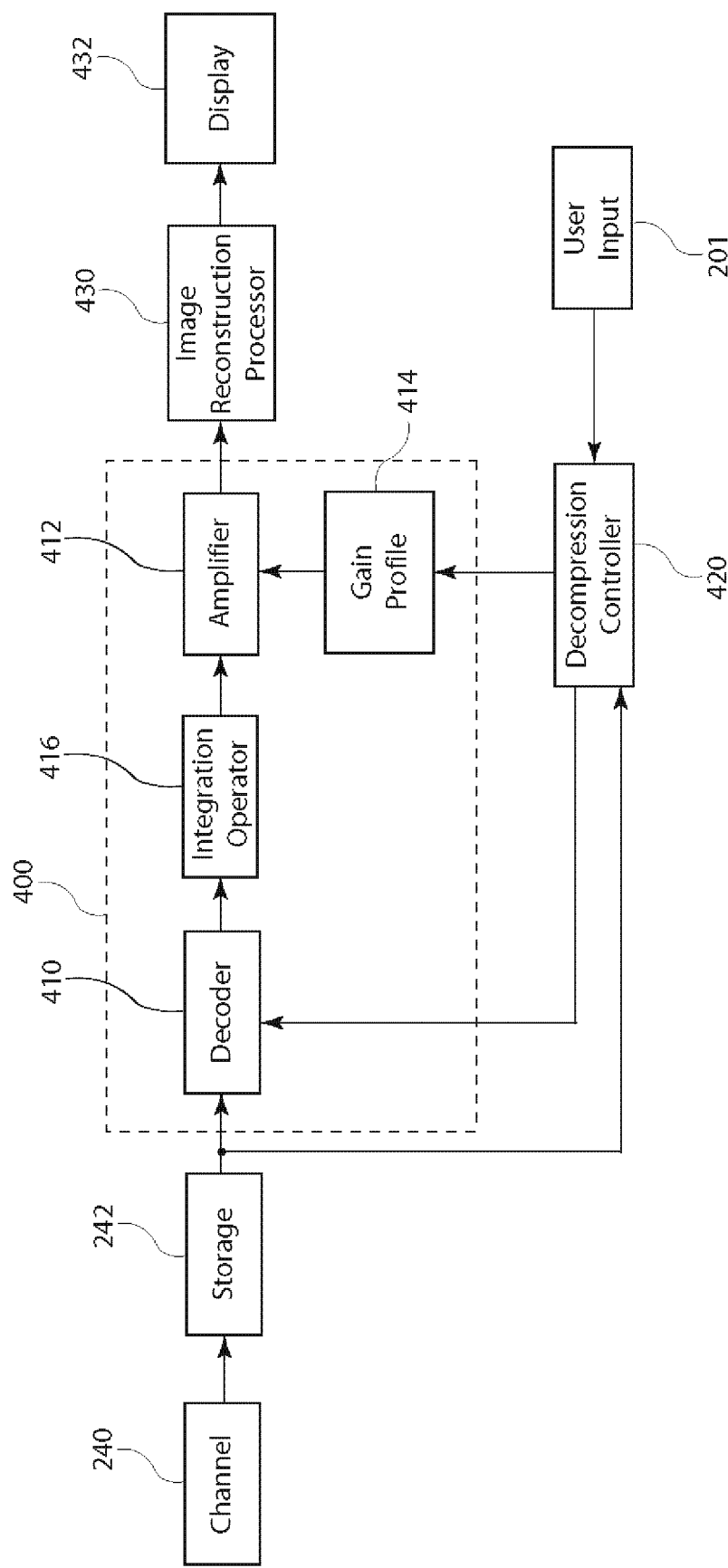
FIG. 8 is a block diagram of decompression for subsequent image reconstruction.

FIG. 8 is a block diagram of decompression for subsequent image reconstruction. After transmission via the channel 240 and optional storage 242, the decompression processor 400 decompresses the compressed samples prior to image reconstruction processing. The image reconstruction processor 430 uses the decompressed samples to compute an image using well-known CT image reconstruction algorithms. The reconstructed image can be presented on display 432. Alternatively, the compressed samples may be stored in a storage device or data storage media prior to decompression by decompression processor 400 and image formation by the image reconstruction processor 430. The decompression controller 420 provides compression control parameters to the decompression processor 400. When compression control parameters are included in the compressed data, they are recovered by the decompression controller 420. The decompression controller 420 optionally receives user input 201.

The decompression processor 400 depicted in FIG. 8 corresponds to the compression processor 200 of FIG. 4 that applies differential encoding. The decompression processor 400 applies differential decoding to the input compressed samples. The decoder 410 unpacks the compressed samples by applying block floating point decoding, Huffman decoding or other unpacking appropriate for the encoding applied by the encoder 212. Since the compression processor 200 includes the difference operator 216, as described with respect to FIG. 4, the unpacked samples correspond to decoded difference samples. The decompression processor 400 applies the integration operator 416 to form reconstructed attenuated samples. The integration operator 416 applies first or higher order integration to invert the operations of the difference operator 216, in accordance with one of the following:

1) Integrating the decoded difference samples in the same line, or row, to reconstruct consecutive attenuated samples, or integrating column by column;
2) Integrating the decoded difference samples in corresponding positions in multiple lines, or integrating row by row, to reconstruct attenuated samples corresponding to consecutive lines of the same set of projection data;
3) Integrating decoded difference samples in corresponding positions in multiple arrays, or integrating array by array, to reconstruct arrays of attenuated samples corresponding to consecutive sets of projection data.

Alternatively, for the compression processor 200 of FIG. 2 that does not include differential encoding, the decompression processor 400 would bypass or not include the integration operator 416. The decoder 410 unpacks the compressed samples by applying block floating point decoding, Huffman decoding or other unpacking appropriate for the encoding applied by the encoder 212. In this case, the decoded samples correspond to the reconstructed attenuated samples and are input to the amplifier 412.

The amplifier 412 applies the gain profile 414 to the reconstructed attenuated samples to form the decompressed samples. For the attenuation profile function g(j) of equation (1) the corresponding gain profile function f(j) is, $$f(j) = 2^{y(j)} y(j) \geq 0 \quad (17)$$

The amplifier 412 does not restore the original sample values of array 160 because the truncation or rounding that occurs from attenuation is irreversible. Since the gain profile function f(j) does not provide the exact inverse of the attenuation profile function g(j), the resulting compression/decompression is lossy. However, the decompressed samples have the same number of bits per sample and the same dynamic range as the original samples.

The amplifier 412 applies a gain profile 414, such as that of equation (17) by multiplying the reconstructed attenuated samples by the corresponding gain values, f(j)≧1. The gain values for the gain profile 414 can be stored in a lookup table in memory and provided to the amplifier 412. Alternatively, the amplifier 412 can calculate the gain values from parameters representing the gain profile 414. A simple embodiment of the amplifier 412 includes left shifting the samples by a number of bits corresponding to the gain values and setting the additional least significant bits to zero or dithered values. A left shift corresponds to a multiplication by two. When the gain profile 414 represented by f(j) is an exponential function of base 2, as in equation (17), the exponent function y(j) can be truncated or rounded to determine a whole number of left shifts. The left shift values corresponding to the gain profile 414 can be stored in a lookup table or calculated by the amplifier 412 from parameters of the gain profile 414. Alternatively, when the value y(j) in equation (7) is not an integer, the fractional part of y(j) can be applied using a multiplier. The image reconstruction processor 430 reconstructs an image from the decompressed samples.

When the compression processing includes defining the boundaries of the attenuation profile 214 with respect to edge samples of the projection data, such as described with respect to FIG. 7, the decompression processor 400 also decodes the boundary information included with the compressed samples. The amplifier 412 applies the gain profile 414 within the appropriate boundaries of the reconstructed attenuated samples.

The compression processor 200 applies simple operations that can compress samples output from the ADCs of the DAS 130 in real time. The attenuator 210 can include a multiplier, divider and/or right shift operator. A lookup table stored in memory can supply the attenuation values for the attenuator 210. The difference operator 216 includes one or more subtractors. Multiple subtractors operating in parallel can calculate line-by-line or array-by-array differences. An encoder 212 applying block floating point encoding uses comparators, subtractors and lookup tables. An encoder 212 applying Huffman encoding uses a lookup table to assign a code to the attenuated sample value or difference value. The bit rate monitor 222 and compression controller 220 use addition, subtraction and multiplication operations. The decompression processor 400 applies simple operations to decompress the compressed samples in real time. The decoder 410 includes lookup tables and adders for block floating point decoding. The integration operator 416 includes one or more adders for integrating the decoded samples. The amplifier 412 can include a multiplier or a left shift operator. The values of the gain profile 414 can be stored in a lookup table in memory.

The present invention can be implemented as a compression subsystem in the DAS 130. In an application specific integrated circuit (ASIC) for the DAS 130 that includes an ADC and the compression subsystem can be integrated into the ASIC to compress samples output from the ADC. In an alternative implementation, the compression subsystem is embodied in a separate device that is coupled to the output of an ADC chip in the DAS 130. The device can be implemented as an ASIC, a field programmable gate array (FPGA), or a programmable processor, such as a digital signal processor (DSP), microprocessor, microcontroller, multi-core CPU (such as IBM Cell), or graphics processing unit (GPU; such as Nvidia GeForce). Depending on the CT system architecture, the decompression subsystem may be incorporated into the same device as or a different device from the image reconstruction processor. The decompression subsystem could be implemented in an ASIC, FPGA or programmable processor. The user interface can be incorporated into the control console for the CT system using programming techniques well known in the art.

While embodiments of the present invention are described herein using examples related to medical applications of computed tomography, the present invention is not limited to medical applications. Embodiments of the present invention can also be adapted for use in industrial computed tomography. In industrial computed tomography systems, the apparatus that moves the object, x-ray source and detector array is designed for the types of objects being tested. During a scan of the object, the relative motion of the object, x-ray source and detector array results in several views that generate sets of projection data to which embodiments of the present invention can be applied.

While the preferred embodiments of the invention have been illustrated and described, it will be clear that the invention is not limited to these embodiments only. Numerous modifications, changes, variations, substitutions and equivalents will be apparent to those skilled in the art, without departing from the spirit and scope of the invention, as described in the claims.

We claim:

1. A method for compressing projection data in a computed tomography system that includes a plurality of sensors providing a plurality of sensor measurements to form one or more sets of projection data for an object, wherein each set includes an array of samples of the projection data, the array having at least one line of samples, wherein each sample has a position in the array indicated by a sample coordinate, the method comprising:

detecting a first edge sample and a second edge sample in the line of the array;

determining a first boundary coordinate in the line based on the first edge sample and a second boundary coordinate in the line based on the second edge sample;

compressing samples having sample coordinates between the first boundary coordinate and the second boundary coordinate to form compressed samples; and encoding the first and second boundary coordinates to form encoded boundaries included with the compressed samples, wherein the step of detecting comprises:

calculating differences between consecutive samples in the line of the array to form difference samples, each difference sample having a positive value or a negative value; and comparing the positive difference samples to a positive threshold and the negative difference samples to a negative threshold to determine the first edge sample and the second edge sample, wherein the step of detecting further comprises determining the positive threshold and the negative threshold, further comprising:
setting the positive threshold to an initial positive value and the negative threshold to an initial negative value;
applying the step of comparing to determine a number of positive difference samples greater than the positive threshold and a number of negative difference samples less than the negative threshold;
reducing respective magnitudes of the positive threshold and the negative threshold, if the respective number of difference samples is zero; and
repeating the steps of comparing and reducing until the respective number of difference samples is greater than zero to produce the positive threshold and the negative threshold.

2. The method of claim 1, wherein values of the projection data corresponding to empty space are less than the values of the projection data corresponding to an object being scanned, wherein the step of comparing further comprises:
selecting the positive difference samples greater than the positive threshold to form a first set of candidate edge samples;
selecting the negative difference samples less than the negative threshold to form a second set of candidate edge samples;
selecting the candidate edge sample from the first set having a lowest sample coordinate to be the first edge sample; and
selecting the candidate edge sample from the second set having a highest sample coordinate to be the second edge sample.

3. The method of claim 1, wherein values of the projection data corresponding to empty space are greater than the values of the projection data corresponding to an object being scanned, wherein the step of comparing further comprises:
selecting the difference samples greater than the positive threshold to form a first set of candidate edge samples;
selecting the difference samples less than the negative threshold to form a second set of candidate edge samples;
selecting the candidate edge sample from the first set having a highest sample coordinate to be the first edge sample; and
selecting the candidate edge sample from the second set having a lowest sample coordinate to be the second edge sample.

4. The method of claim 1, wherein the step of compressing further comprises:
encoding the difference samples corresponding to the sample coordinates between the first boundary coordinate and the second boundary coordinate to form the compressed samples.

5. The method of claim 4, further comprising:
decoding the encoded boundaries to recover the first boundary coordinate and the second boundary coordinate;
decoding the compressed samples to produce decoded difference samples corresponding to the sample coordinates between the first boundary coordinate and the second boundary coordinate; and
integrating the decoded difference samples to form decompressed samples.

6. The method of claim 1, further comprising:
transmitting the compressed samples over a communication channel of a slip ring interface in the computed tomography system.

7. The method of claim 1, further comprising:
decoding the encoded boundaries to recover the first boundary coordinate and the second boundary coordinate; and
decompressing the compressed samples corresponding to the sample coordinates between the first boundary coordinate and the second boundary coordinate for each line to form decompressed samples.

8. The method of claim 7, further comprising providing the decompressed samples and the first and second boundary coordinates for each line to an image reconstruction processor for producing a spatial domain.

9. A method for compressing projection data in a computed tomography system that includes a plurality of sensors providing a plurality of sensor measurements to form one or more sets of projection data for an object, wherein each set includes an array of samples of the projection data, the array having at least one line of samples, wherein each sample has a position in the array indicated by a sample coordinate, the method comprising:
detecting a first edge sample and a second edge sample in the line of the array;
determining a first boundary coordinate in the line based on the first edge sample and a second boundary coordinate in the line based on the second edge sample;
compressing samples having sample coordinates between the first boundary coordinate and the second boundary coordinate to form compressed samples; and
encoding the first and second boundary coordinates to form encoded boundaries included with the compressed samples, wherein the step of detecting comprises:
calculating differences between consecutive samples in the line of the array to form difference samples, each difference sample having a positive value or a negative value; and
comparing the positive difference samples to a positive threshold and the negative difference samples to a negative threshold to determine the first edge sample and the second edge sample, and
wherein the step of compressing further comprises:
attenuating the samples corresponding to the sample coordinates between the first boundary coordinate and the second boundary coordinate in accordance with an attenuation profile to form attenuated samples, wherein the attenuation profile is a function of the sample coordinates; and
encoding the attenuated samples to produce the compressed samples;
wherein the step of detecting further comprises determining the positive threshold and the negative threshold, further comprising:
setting the positive threshold to an initial positive value and the negative threshold to an initial negative value;
applying the step of comparing to determine a number of positive difference samples greater than the positive threshold and a number of negative difference samples less than the negative threshold;
reducing respective magnitudes of the positive threshold and the negative threshold, if the respective number of difference samples is zero; and
repeating the steps of comparing and reducing until the respective number of difference samples is greater than zero to produce the positive threshold and the negative threshold.

10. The method of claim 9, further comprising:
decoding the encoded boundaries to recover the first boundary coordinate and the second boundary coordinate;

decoding the compressed samples to produce reconstructed attenuated samples corresponding to the sample coordinates between the first boundary coordinate and the second boundary coordinate; and amplifying the reconstructed attenuated samples in accordance with a gain profile, wherein the gain profile corresponds to the attenuation profile, to form decompressed samples.

11. The method of claim 9, wherein values of the projection data corresponding to empty space are greater than the values of the projection data corresponding to an object being scanned, wherein the step of comparing further comprises:

selecting the difference samples greater than the positive threshold to form a first set of candidate edge samples;

selecting the difference samples less than the negative threshold to form a second set of candidate edge samples;

selecting the candidate edge sample from the first set having a lowest sample coordinate to be the first edge sample; and selecting the candidate edge sample from the second set having a highest sample coordinate to be the second edge sample.

12. The method of claim 9, wherein values of the projection data corresponding to empty space are greater than the values of the projection data corresponding to an object being scanned, wherein the step of comparing further comprises:

selecting the difference samples greater than the positive threshold to form a first set of candidate edge samples;

selecting the difference samples less than the negative threshold to form a second set of candidate edge samples;

selecting the candidate edge sample from the first set having a highest sample coordinate to be the first edge sample; and selecting the candidate edge sample from the second set having a lowest sample coordinate to be the second edge sample.

13. The method of claim 9, further comprising:

transmitting the compressed samples over a communication channel of a slip ring interface in the computed tomography system.

14. The method of claim 9, further comprising:

decoding the encoded boundaries to recover the first boundary coordinate and the second boundary coordinate; and decompressing the compressed samples corresponding to the sample coordinates between the first boundary coordinate and the second boundary coordinate for each line to form decompressed samples.

15. The method of claim 14, further comprising providing the decompressed samples and the first and second boundary coordinates for each line to an image reconstruction processor for producing a spatial domain image.

16. An apparatus for compressing projection data in a computed tomography system that includes a plurality of sensors providing a plurality of sensor measurements to form one or more sets of projection data for an object, wherein each set of projection data represents a portion of a projection domain and includes an array of samples of the projection data, the array having at least one line of samples, wherein each sample has a position in the array indicated by a sample coordinate, the apparatus comprising:

a compression subsystem coupled to receive the samples of the projection data and providing compressed samples to a data transfer interface, the compression subsystem further comprising:

an edge detector applied to samples in the line of the array, wherein the edge detector determines a first edge sample and a second edge sample in the line of samples, and sets a first boundary coordinate and a second boundary coordinate based on the first edge sample and the second edge sample, respectively;

a compressor that compresses the samples corresponding to the sample coordinates between the first boundary coordinate and the second boundary coordinate to form the compressed samples; and a boundary encoder that encodes the first boundary coordinate and the second boundary coordinate to include with the compressed samples, wherein the edge detector further comprises:

a difference calculator that calculates a plurality of differences between samples in the line of the array to form difference samples, each difference sample having a positive value or a negative value; and a threshold operator applied to the positive difference samples and the negative difference samples to produce the first edge sample and the second edge sample, wherein the compressor further comprises:

an attenuator that attenuates the samples corresponding to the sample coordinates between the first boundary coordinate and the second boundary coordinate in accordance with an attenuation profile to form attenuated samples, wherein the attenuation profile is a function of the sample coordinates; and an encoder that encodes the attenuated samples to produce the compressed samples; and further including logic to determine a threshold value for the threshold operator, using a process including:

setting a threshold magnitude to an initial value;

using results from the difference calculator to determine a number of difference samples having magnitudes exceeding the threshold magnitude;

reducing the threshold magnitude, if the number of difference samples is zero; and repeating the steps of using the results from the difference calculator and reducing the threshold magnitude until the respective number of difference samples is greater than zero to produce the threshold value.

17. The apparatus of claim 16, wherein the computed tomography system further comprises a decompression subsystem coupled to receive the compressed samples from the data transfer interface and producing decompressed samples, the decompression subsystem further comprising:

a boundary decoder that decodes the first boundary coordinate and the second boundary coordinate from the compressed samples;

a decoder that decodes the compressed samples corresponding to the sample coordinates between the first boundary coordinate and the second boundary coordinate to produce reconstructed attenuated samples; and an amplifier that increases magnitudes of the reconstructed attenuated samples in accordance with a gain profile to form the decompressed samples, wherein the gain profile corresponds to the attenuation profile.

18. The apparatus of claim 16, wherein the compression subsystem is implemented in a field programmable gate array (FPGA), an application specific integrated circuit (ASIC) or a programmable processor.

19. The apparatus of claim 16, wherein the compression subsystem is located in a rotating unit of a gantry of the computed tomography system.

20. The apparatus of claim 16, wherein values of the projection data corresponding to empty space are less than the values of the projection data corresponding to an object being scanned, wherein the threshold operator further comprises:
- a first comparator to compare the positive difference samples to a positive threshold to form a first set of candidate edge samples having differences greater than a positive threshold; and
- a second comparator to compare the negative difference samples to a negative threshold to form a second set of candidate edge samples having differences less than a negative threshold, the edge detector further comprising:
- an edge selector receiving the first set and the second set, wherein the edge selector selects the candidate edge sample of the first set having a lowest sample coordinate to be the first edge sample and selects the candidate edge sample of the second set having a highest sample coordinate to be the second edge sample.

21. The apparatus of claim 16, wherein values of the projection data corresponding to empty space are greater than the values of the projection data corresponding to an object being scanned, wherein the threshold operator further comprises:
- a first comparator to compare the positive difference samples to a positive threshold to form a first set of candidate edge samples having differences greater than a positive threshold; and
- a second comparator to compare the negative difference samples to a negative threshold to form a second set of candidate edge samples having differences less than a negative threshold, the edge detector further comprising:
- an edge selector receiving the first set and the second set, wherein the edge selector selects the candidate edge sample of the first set having a highest sample coordinate to be the first edge sample and selects the candidate edge sample of the second set having a lowest sample coordinate to be the second edge sample.

22. The apparatus of claim 16, wherein the computed tomography system further comprises a decompression subsystem coupled to receive the compressed samples from the data transfer interface and producing decompressed samples, the decompression subsystem further comprising:
- a boundary decoder that decodes the first boundary coordinate and the second boundary coordinate from the compressed samples; and
- a decoder that decodes the compressed samples corresponding to the sample coordinates between the first boundary coordinate and the second boundary coordinate to form the decompressed samples.

23. The apparatus of claim 22, wherein the decompression subsystem provides the first boundary coordinate, the second boundary coordinate and the decompressed samples to an image reconstruction processor.

24. The apparatus of claim 22, wherein the decompression subsystem is implemented in a field programmable gate array (FPGA), an application specific integrated circuit (ASIC) or a programmable processor.

25. The apparatus of claim 22, wherein the decompression subsystem is located in one of the following:
- a stationary unit of a gantry of the computed tomography system; and
- an image reconstruction processor of the computed tomography system.

26. The apparatus of claim 16, wherein the compression subsystem is located in a rotating unit of a gantry of the computed tomography system.

* * * * *